United States Patent

Paulseth

[11] Patent Number: 4,556,054
[45] Date of Patent: Dec. 3, 1985

[54] ANKLE ORTHOSIS

[76] Inventor: Stephen G. Paulseth, 2028 14th St., Apt. E, Santa Monica, Calif. 90405

[21] Appl. No.: 554,063

[22] Filed: Nov. 21, 1983

[51] Int. Cl.[4] .............................................. A61F 3/00
[52] U.S. Cl. .................................. 128/80 H; 128/166
[58] Field of Search ...................... 128/80 R, 80 H, 166

[56] References Cited

U.S. PATENT DOCUMENTS

| 112,952 | 3/1871 | Niswander | 128/166 |
|---|---|---|---|
| 130,639 | 8/1872 | Howe | 128/166 |
| 713,912 | 11/1902 | Nathan | 128/166 |
| 1,549,382 | 8/1925 | Riddell | 128/166 |
| 2,847,991 | 8/1958 | Andrews | 128/80 |
| 3,387,305 | 6/1968 | Shafer | 128/80 |
| 3,490,450 | 1/1970 | Gardner | 128/166 |
| 3,527,209 | 9/1970 | Baker | 128/80 |
| 3,834,377 | 9/1974 | Lebold | 128/80 H |
| 4,102,337 | 7/1978 | Golia | 128/80 |
| 4,133,311 | 1/1979 | Karczewski | 128/166 |

Primary Examiner—Curtis R. Davis
Attorney, Agent, or Firm—R. Craig Armstrong

[57] ABSTRACT

An ankle orthosis useful for the prevention and/or rehabilitation of inversion injuries is disclosed. The orthosis includes a cuff adapted for fastening around the leg above the ankle, a foot plate for positioning beneath the foot, and connecting means extending down the lateral side of the orthosis. Resilient or elastic means may be employed in conjunction with non-elastic means to produce any desired combination of elastic and non-elastic restriction of ankle inversion.

5 Claims, 6 Drawing Figures

ANKLE ORTHOSIS

BACKGROUND OF THE INVENTION

1. Field of the Invention

This invention relates generally to ankle orthoses, and particularly to an ankle orthosis intended to brace or support the ankle against inversion, for the prevention and rehabilitation of inversion injuries.

The great majority of ankle injuries occur to the lateral side as a result of inversion, and ankle injuries caused by inversion are a problem for a great many people, particularly athletes. In many cases, such injuries can become chronic, with each successive injury further weakening the ankle and leading to increased susceptibility to further injury. While the series of hindfoot joints, namely the midtarsal, the subtaler, and the talocrural (ankle) joints, function mainly as a hinge in plantar and dorsi flexion, they do allow some eversion and inversion. The lateral malleolus within the ankle joint tends to prevent excessive eversion unless the eversive force is strong enough to cause its fracture. The medial malleolus, however, will not prevent inversion to the same degree due to its shorter length. The lateral ligaments are also much weaker than their medial counterparts. Inversion injuries are therefore very common.

Accordingly, there is a need for a suitable orthosis to aid in preventing inversion injury, and to assist in the rehabilitation of such injuries. The ideal ankle orthosis should be light, durable, and easy to use. It should permit a certain range of motion in order to allow normal function. In the post-traumatic condition, this range, particularly in the coronal plane, must be controlled to stabilize the joint, provide proprioceptive input, and reduce pain with motion. At the same time the orthosis must allow some movement for functional healing to occur. It should be possible to wear the orthosis within a shoe or boot. There should be resistance to decay of functional effectiveness during exercise.

2. Description of the Prior Art

Most ankle supports in the prior art can be delineated by both their structure and the materials used. There are non-rigid devices such as adhesive tape, with its multiple techniques of application, high top shoes, elastic wraps, and lace-up sleeves and boots. These are designed primarily for the prevention of injury. There are also rigid devices which limit ankle motion drastically. They are typically made of orthoplast, polyethylene and polypropylene, which have little flexibility or functional motion.

One of the most commonly used techniques, in athletics in particular, is the use of tape to wrap the ankle. While such taping offers some psychological protection and some physical protection, its effectiveness is limited. Taping is expensive in the long run, its effectiveness degrades gradually during exercise, and movement of the ankle is restricted generally. Other existing braces, such as those described in U.S. Pat. No. 3,506,000 (Baker), U.S. Pat. No. 3,490,450 (Gardner), and U.S. Pat. No. 3,674,023 (Mann), are generally either too cumbersome or too restrictive of movement, or tend to either hinder or excessively allow a complex range of motion of the ankle.

It is an object of the present invention to provide an ankle orthosis which offers advantages over those in the prior art.

SUMMARY OF THE INVENTION

In accordance with the present invention, there is provided an ankle orthosis which is relatively light, durable, and easy to use. Inversion of the ankle is restricted, with relatively little restriction of plantar and dorsi flexion and eversion. The orthosis may be worn within a boot or shoe, and an elastic wrap may be worn under it to control swelling as well as to provide more support if desired.

The invention includes a cuff adapted for fastening around the leg above the ankle and a foot plate adapted to be positioned beneath the tarsal bones of the foot. Connecting means extend down the lateral side of the ankle between the cuff and the foot plate. The length of the connecting means is selected in relation to the distance between the cuff and the foot plate so as to restrict inversion of the ankle. In embodiments preferred in the case of a relatively healthy ankle, where prevention of injury is the primary desire, resilient or elastic connecting means permit a limited amount of ankle inversion, under restriction, up to a limit beyond which further inversion is substantially prevented. In the situation where an injured or chronically weak ankle is to be rehabilitated, the degree of inversion which is permitted may be reduced considerably or indeed virtually eliminated in embodiments without resilient or elastic means. As will become apparent, there is no single preferred embodiment. The embodiment preferred will depend on the judgment of the orthotist prescribing the ankle orthotic. It will be apparent that virtually any desireable combination of elastic and non-elastic restriction of inversion may be obtained by varying or adjusting the features of the invention.

DESCRIPTION OF THE DRAWINGS

In order that the invention may be more clearly understood, reference will now be made to the accompanying drawings which illustrate alternative embodiments by way of example only, and in which.

DESCRIPTION OF THE PREFERRED EMBODIMENT

Figure 1:
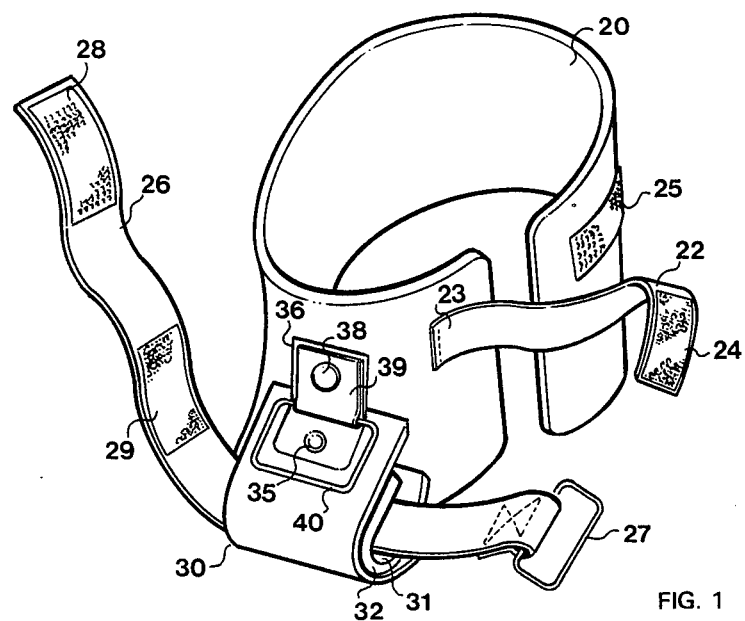
FIG. 1 is a perspective of the cuff portion of an embodiment preferred for most preventative applications.

Referring now to the drawings, the invention and its alternative embodiments will be described in greater detail.

FIG. 1 shows a cuff 20 adapted for fastening around an ankle proximal to the malleoli of the ankle. It is important that the cuff be fastened securely so that in use it cannot slide down the ankle. Accordingly there are several straps provided for fastening the cuff around the ankle, namely a locator strap 22 sewn at one end 23 to the cuff, and a fastening strap 26. The locator strap has a Velcro hook portion 24 which mates with a pile portion 25 on the cuff. The fastening strap 26 has a box ring 27 at one end and Velcro hook and pile portions 28 and 29 respectively. As can be seen from FIG. 3, the fastening strap is wrapped tightly around the ankle with the end opposite the box ring 27 passing through the box ring, and the hook portion 28 mating with the pile portion 29 to secure the strap. Positioning the fastening strap slightly above the malleoli of the ankle is preferable so that downward slippage of the cuff is prevented by virtue of the cuff riding on the malleoli.

The cuff 20 is preferably of a relatively flexible but sturdy material such as Pilite, although any suitable material could of course be used. Depending on the material selected, a liner may or may not be needed to provide wearer comfort. It will of course also be appreciated that any suitable fastening means may be employed, the above-described means being just one of many possible arrangements.

The cuff 20 is provided with a flange 30 which is shaped upwardly and back onto the cuff, defining a channel 31 which serves to locate the fastening strap 26 which passes through it. Lining the channel is a resilient pad 32 of Sorbothane or other suitable resilient material. A rivet 35 passes through a reinforcement panel 36, the flange 30, the cuff 20, and a rear reinforcement panel (not shown) similiar to panel 36, thereby securing these components. Another rivet 38 fastens a tab 39 to the cuff through the reinforcement panels. The tab 39 holds another box ring 40.

The flange 30 and the resilient pad 32 together form a bumper pad 42 protruding outwardly from the cuff. The box ring 40 rests on this bumper pad.

Depending on the material selected for the cuff, the reinforcement panel 36 and its counterpart on the inside of the cuff may of course be unnecessary. It will also be appreciated that the particular arrangement of the rivet 35, the flange 30 and the resilient pad 32 is not essential to this particular embodiment, as long as a resilient bumper pad 42 is somehow created.

Figure 2:
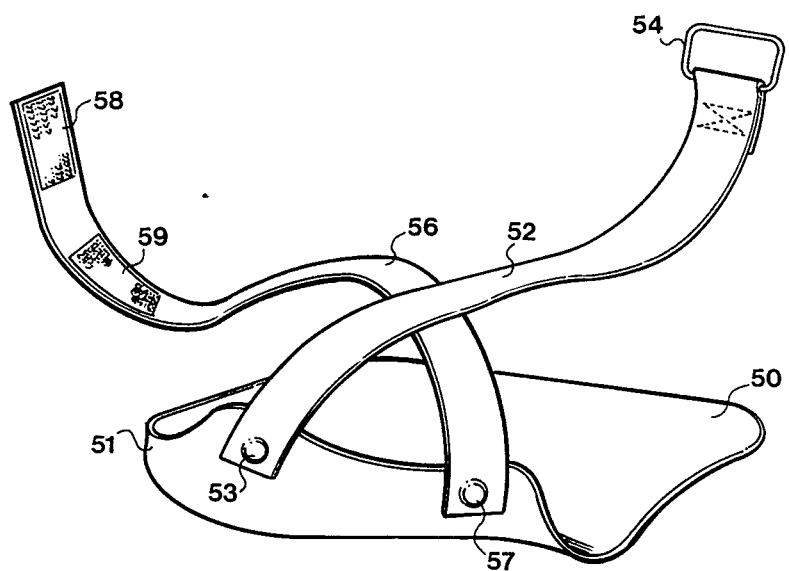
FIG. 2 is a perspective of the foot plate and connecting straps adapted for use with the cuff of FIG. 1.

FIG. 2 shows the other main component of the orthosis of FIG. 1, namely a foot plate 50 and connecting straps. The foot plate is relatively rigid and is of course shaped to be located beneath the foot and beneath the tarsal bones in particular. Raised edges 51 facilitate proper positioning of the foot plate. It will be immediately apparent that the shape of the foot plate is not essential, and in fact a boot or shoe could itself act as the foot plate. Ordinarily, though, the foot plate will be a separate component worn within a shoe or boot and held in place by the shoe or boot. Auxiliary fastening means such as a strap across the top of the foot may be employed if desired.

A first connecting strap 52 is attached at one end to the raised edge 51 at a rearward lateral portion of the foot plate by rivet 53. At the other end is attached a box ring 54. A second connecting strap 56 is attached at one end to the raised edge 51 at a forward lateral portion of the foot plate by rivet 57. This second connecting strap has Velcro hook and pile portions 58 and 59 respectively.

Figure 3:
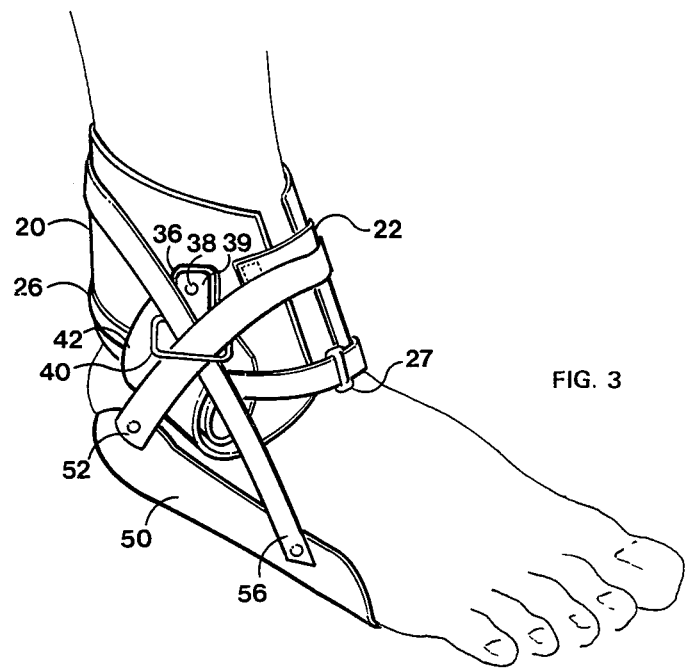
FIG. 3 is a perspective of the orthosis of FIGS. 1 and 2, seen as installed on an ankle.

FIG. 3 shows how the orthosis is assembled and installed on an ankle. With the cuff installed and the foot plate positioned beneath the foot, the connecting straps 52 and 56 are routed upwardly through the box ring 40, crossing over each other in the box ring. The connecting straps should preferably but not essentially pass through the box ring from inside out. It is not material whether connecting strap 52 overlies connecting strap 56 or vice versa. From the box ring 40, connecting strap 52 passes around the front of the cuff 20 and connecting strap 56 passes around the rear of the cuff. The straps are tightened and attached to each other on the medial side of the cuff by passing the end of strap 56 through the box ring 54 and mating the Velcro hook portion 58 with pile portion 59. It will be apparent that when the connecting straps 52 and 56 are so attached, inversion of the ankle is restricted. This restriction would be virtually complete in the absence of the bumper pad 42, so that only a minimal amount of ankle inversion would be possible before the tightness of the straps prevented further inversion. Thus where any significant degree of inversion is undesireable, as for example in the case of an injured or chronically weak ankle, the bumper pad 42 can be omitted. Otherwise, the bumper pad operates to permit a certain amount of ankle inversion, under restriction. Since the connecting straps 52 and 56 overlie the bumper pad, which protrudes outwardly from the cuff, they can only become completely taut by compressing the bumper pad. Thus as inversion occurs, the connecting straps tighten and compress the bumper pad. The resilience of the bumper pads of course produces progressive resistance to such inversion. Eventually enough inversion occurs to fully compress the bumper pad, and further inversion is prevented.

It is apparent that varying the size and resilience of the bumper pad will result in different inversion resistance and in different inversion resistance thresholds, thus permitting custom treatment of a wide range of ankle inversion problems, ranging from pure prevention to rehabilitation of severe injuries.

Figure 4:
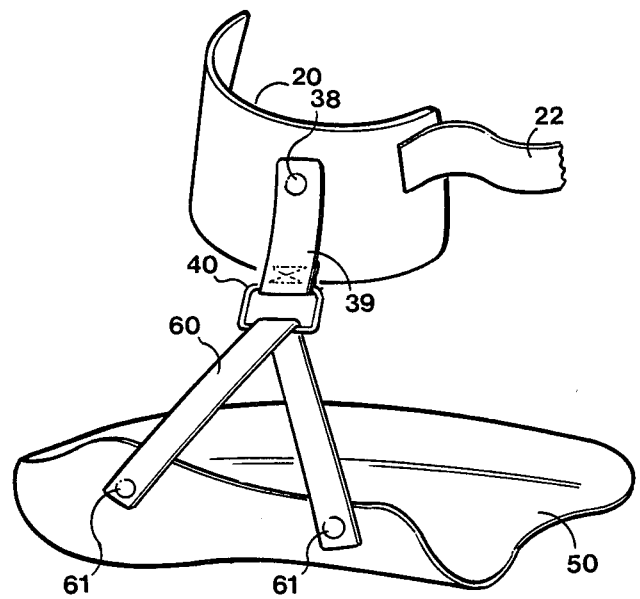
FIG. 4 is a drawing of an alternative connecting means.

FIG. 4 illustrates an alternative connecting strap arrangement, in which a single connecting strap 60 is attached to the foot plate 50 by rivets 61. The connecting strap simply loops through the box ring 40 and back down to the foot plate in this embodiment. This embodiment may be useful where it is not necessary that the orthosis be adjustable, or alternatively means may be provided for permitting adjustment of the length of the connecting strap 60 or of the tab 39.

Yet another embodiment, though not illustrated, may be readily envisioned from FIG. 4. The bumper pad 42 may be eliminated and the elasticity may be provided by employing an elastic material for the connecting strap 60. The tab 39 is preferably adjustable in such an embodiment. To prevent inversion beyond the desired limit, a non-elastic strap (not shown) connects the lateral side of the cuff to the lateral side of the foot plate. The length of this non-elastic strap is selected such that a certain amount of inversion is permitted, under the control of the elastic connecting strap 60, before the non-elastic strap becomes taut and thereby prevents further inversion.

Figure 5:
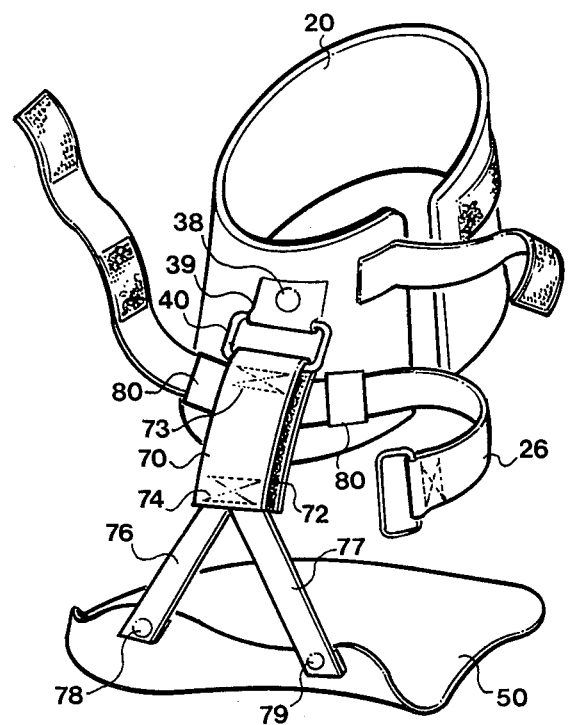
FIG. 5 is a perspective of an alternative embodiment of the invention.

FIG. 5 illustrates yet another embodiment of the invention. In this embodiment, there is no bumper pad, the elasticity being provided by an elastic strap 70. A rivet 38 secures a tab 39 to the lateral side of the cuff 20. The length of the tab 39 is preferably adjustable by any suitable means (not shown). A box ring 40 is held by the tab 39. The elastic strap 70 loops over the box ring 40 and the two ends of the strap extend downwardly. Between the two elastic layers thus formed is a non-elastic strap 72, sewn together with the two elastic layers at each end of the non-elastic strap, the length of the non-elastic strap being somewhat greater than the distance between the upper and lower sewing points 73 and 74. Also sewn into the straps at the lower sewing point 74 are the ends of two non-elastic straps 76 and 77, their other ends being attached to the lateral side of the foot plate by rivets 78 and 79 respectively.

In this embodiment, inversion is permitted under the control and progressive resistance of the elastic strap 70, until sufficient stretching of the elastic strap has taken place to straighten the non-elastic strap 72, whereupon further inversion is substantially prevented.

It will be noted that in this and other embodiments with no bumper pad and hence no channel for the fastening strap 26 to ride in, it may be adviseable to employ such means as loops 80 to guide the fastening strap.

Figure 6:
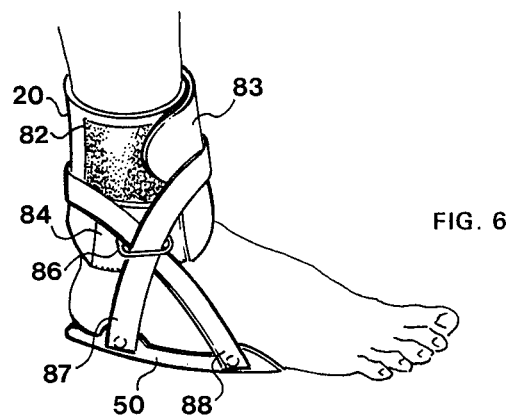
FIG. 6 is a perspective of yet another alternative embodiment of the invention, seen as installed on an ankle.

Referring finally to FIG. 6, yet another embodiment is illustrated. A neoprene cuff 20 is seen installed around an ankle. The cuff has a velcro pile portion 82 on the lateral side, to which is mated a hook portion 83 sewn to the medial side of the cuff and passing around the front of the ankle. A sorbothane fulcrum pad or bumper 84 is sewn into the lateral side of the cuff. A box ring 86 is attached to overlie the bumper. Connecting straps 87 and 88 rise from the foot plate 50, cross over each other in the box ring 86, and pass around to the medial side of the ankle where they mate with each other, one being provided with a velcro hook portion and the other being provided with a velcro pile portion.

In all of the embodiments of the invention, it is preferable that the box ring 40 should approximately overlie the talocrural joint axis, and the connecting straps (52 and 56 in FIGS. 2 and 3; 60 in FIG. 4; 76 and 77 in FIG. 5; 87 and 88 in FIG. 6) should roughly overlie the calcaneal-fibular ligament and the anterior talofibular ligament respectively, for optimum restriction against inversion and lack of restriction against plantar and dorsi flexion.

Many other modifications and alternative embodiments are obvious in view of the above and yet are within the broad scope of the invention as described and claimed, and indeed it is an advantage of the present invention that such modifications and alternative embodiments are possible so that the orthosis is suitable for many situations.

What I claim as my invention is:

1. An ankle orthosis adapted for installation on an ankle, comprising:
   a cuff, adapted for fastening around the leg above the ankle;
   a foot plate, adapted to be positioned beneath the tarsal bones of the foot;
   means connecting the cuff and the foot plate positioned so as to extend down the lateral side of the ankle when the orthosis is worn on the ankle, the length of said connecting means in relation to the distance between the cuff and the foot plate being such as to restrict inversion of the ankle, said connecting means comprising a non-elastic strap; and
   a resilient bumper attached to the lateral side of the cuff and protruding outwardly therefrom, said connecting means overriding and being displaced by said bumper such that said non-elastic strap can only be straightened by compressing said bumper between said connecting means and the ankle, whereby ankle inversion is progressively resisted by virtue of the resilience of the bumper, and whereby ankle inversion is substantially prevented once said progressive resistance has been overcome and said non-elastic strap has been straightened.

2. An ankle orthosis as recited in claim 1, in which said connecting means comprise:
   a ring connected to a lateral portion of the cuff;
   a first strap connected to a rearward lateral portion of the foot plate and extending upwardly and forwardly through said ring; and
   a second strap connected to a forward lateral portion said foot plate and extending rearwardly and upwardly through said ring; said first and second straps thence extending forwardly and rearwardly respectively and around the ankle and being adapted for fastening to each other on the medial side of the ankle.

3. An ankle orthosis as recited in claim 1, in which said connecting means comprise:
   a ring connected to a lateral portion of the cuff; and
   a strap connected at one end to a rearward lateral portion of the foot plate, extending forwardly and upwardly through the ring and thence downwardly and forwardly, and connected at its other end to a forward lateral portion of the foot plate.

4. An ankle orthosis adapted for installation on an ankle, comprising:
   a cuff, adapted for fastening around the leg above the ankle;
   a foot plate, adapted to be positioned beneath the tarsal bones of the foot;
   means connecting the cuff and the foot plate positioned so as to extend down the lateral side of the ankle when the orthosis is worn on the ankle, the length of said connecting means in relation to the distance between the cuff and the foot plate being such as to restrict inversion of the ankle, said connecting means comprising a ring connected to a lateral portion of the cuff, an elastic strap connected at one end to a rearward lateral portion of the foot plate, extending forwardly and upwardly through the ring and thence downwardly and forwardly, and connected at its other end to a forward lateral portion of the foot plate, whereby the restriction against inversion increases progressively as and a non-elastic strap connected between the cuff and the foot inversion occurs and the strap stretches, plate on the lateral side of the ankle, whereby inversion is elastically restricted by the elastic strap until sufficient inversion has occurred to tauten the non-elastic strap, whereupon further inversion is substantially prevented.

5. An ankle orthosis adapted for installation on an ankle, comprising:
   a cuff, adapted for fastening around the leg above the ankle;
   a foot plate, adapted to be positioned beneath the tarsal bones of the foot;
   means connecting the cuff and the foot plate positioned so as to extend down the lateral side of the ankle when the orthosis is worn on the ankle, the length of said connecting means in relation to the distance between the cuff and the foot plate being such as to restrict inversion of the ankle, said connecting means comprising a non-elastic strap connected between the cuff and the foot plate; and a length of elastic strap attached at its ends to points on said non-elastic strap which are farther apart than the length of the elastic strap, whereby the non-elastic strap can only be tautened by overcoming the elastic resistance of the elastic strap; whereby inversion is progressively restricted as inversion occurs and the elastic strap stretches and inversion is substantially prevented once the non-elastic strap tautens.

\* \* \* \* \*